(12) United States Patent
Cao et al.

(10) Patent No.: US 10,261,019 B2
(45) Date of Patent: *Apr. 16, 2019

(54) BIOSENSOR

(71) Applicant: Shenzhen Genorivision Technology Co., Ltd., Shenzhen (CN)

(72) Inventors: Peiyan Cao, Shenzhen (CN); Yurun Liu, Shenzhen (CN)

(73) Assignee: SHENZHEN GENORIVISION TECHNOLOGY CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/122,489

(22) PCT Filed: Apr. 22, 2015

(86) PCT No.: PCT/CN2015/077142
§ 371 (c)(1),
(2) Date: Aug. 30, 2016

(87) PCT Pub. No.: WO2016/168996
PCT Pub. Date: Oct. 27, 2016

(65) Prior Publication Data
US 2018/0095039 A1    Apr. 5, 2018

(51) Int. Cl.
*G01N 21/64* (2006.01)
*G01J 3/44* (2006.01)
(Continued)

(52) U.S. Cl.
CPC ........ *G01N 21/6486* (2013.01); *G01J 3/0208* (2013.01); *G01J 3/0262* (2013.01);
(Continued)

(58) Field of Classification Search
None
See application file for complete search history.

(56) References Cited

U.S. PATENT DOCUMENTS 3,787,745 A    1/1974  Wulms
5,698,397 A   12/1997  Zarling et al.
(Continued)

FOREIGN PATENT DOCUMENTS

CN    101848757 A    9/2010
CN    103223357 A    7/2013
(Continued)

OTHER PUBLICATIONS

Balsam J. et al., Modeling and design of micromachined optical Söller collimators for lensless CCD-based fluorometry. Analyst, Aug. 21, 2012, vol. 137, pp. 5011-5017.
(Continued)

*Primary Examiner* — Robert T. Crow
(74) *Attorney, Agent, or Firm* — Na Xu; IPro, PLLC

(57) ABSTRACT

Disclosed herein is an apparatus comprising: a plurality of locations configured to have probes attached thereto, wherein interaction between the probes and an analyte generates a signal; an optical system comprising a plurality of collimators; a sensor comprising a plurality of pixels configured to detect the signal; wherein the collimators are configured to essentially prevent light from passing if a deviation of a propagation direction of the light from an optical axis of the collimators is greater than a threshold.

13 Claims, 24 Drawing Sheets

(51) Int. Cl.
*G01J 3/02* (2006.01)
*G01J 3/28* (2006.01)
*G01N 33/543* (2006.01)
*G01N 33/68* (2006.01)
*H01J 29/96* (2006.01)
*H01J 31/50* (2006.01)
*G01N 21/76* (2006.01)
*G01J 3/12* (2006.01)

(52) U.S. Cl.
CPC .......... *G01J 3/0291* (2013.01); *G01J 3/2803* (2013.01); *G01J 3/4406* (2013.01); *G01N 21/6428* (2013.01); *G01N 21/6454* (2013.01); *G01N 33/54373* (2013.01); *G01N 33/6875* (2013.01); *H01J 29/96* (2013.01); *H01J 31/501* (2013.01); *G01J 2003/1213* (2013.01); *G01N 21/76* (2013.01); *G01N 2021/6478* (2013.01); *G01N 2201/0644* (2013.01)

(56) References Cited

U.S. PATENT DOCUMENTS

| | | | |
|---|---|---|---|
| 6,287,871 | B1 | 9/2001 | Herron et al. |
| 6,297,489 | B1 | 10/2001 | Suyama et al. |
| 2005/0074784 | A1 | 4/2005 | Vo-Dinh |
| 2006/0068490 | A1* | 3/2006 | Tang ............... B01F 5/0603 435/287.2 |
| 2006/0202129 | A1* | 9/2006 | Niclass ............... G01T 1/248 250/370.14 |
| 2007/0036511 | A1* | 2/2007 | Lundquist ......... G01J 3/2803 385/147 |
| 2008/0265769 | A1 | 10/2008 | Contarino et al. |
| 2009/0315443 | A1 | 12/2009 | Sullivan et al. |
| 2010/0068825 | A1* | 3/2010 | Breitling ......... G01N 21/6454 436/518 |
| 2010/0140460 | A1 | 6/2010 | Rigneault et al. |
| 2011/0053799 | A1 | 3/2011 | Abiko et al. |
| 2012/0148205 | A1* | 6/2012 | Park ................ H01L 27/14621 385/119 |
| 2012/0170114 | A1 | 7/2012 | Domash et al. |
| 2013/0157882 | A1* | 6/2013 | Quan .................... G01N 21/77 506/9 |
| 2013/0196360 | A1 | 8/2013 | Yeo et al. |
| 2014/0256057 | A1 | 9/2014 | Ozawa et al. |
| 2014/0274746 | A1 | 9/2014 | Khurana et al. |
| 2014/0295577 | A1 | 10/2014 | Matsuzawa et al. |
| 2015/0079596 | A1 | 3/2015 | Eltoukhy et al. |

FOREIGN PATENT DOCUMENTS

| | | | |
|---|---|---|---|
| CN | 103296035 | A | 9/2013 |
| CN | 103857997 | A | 6/2014 |
| DE | 102008011793 | A1 | 9/2009 |
| JP | 2002243908 | A | 8/2002 |
| JP | 2006071417 | A | 3/2006 |
| JP | 2008537131 | A | 9/2008 |
| JP | 2008233251 | A | 10/2008 |
| JP | 2008538312 | A | 10/2008 |
| JP | 2010014824 | A | 1/2010 |
| JP | 2011158665 | A | 8/2011 |
| JP | 2013088378 | A | 5/2013 |
| JP | 2013092393 | A | 5/2013 |
| JP | 2014503081 | A | 2/2014 |
| JP | 2016528496 | A | 9/2016 |
| WO | 2011115030 | A1 | 9/2011 |
| WO | WO 2013/061529 | A1 * | 5/2013 ............. G01N 21/64 |
| WO | 2015015493 | A3 | 3/2015 |

OTHER PUBLICATIONS

Homola J. et al., Spectral surface plasmon resonance biosensor for detection of staphylococcal enterotoxin B in milk. International Journal of Food Microbiology, May 5, 2002, vol. 75, No. 1-2, pp. 61-69.

* cited by examiner

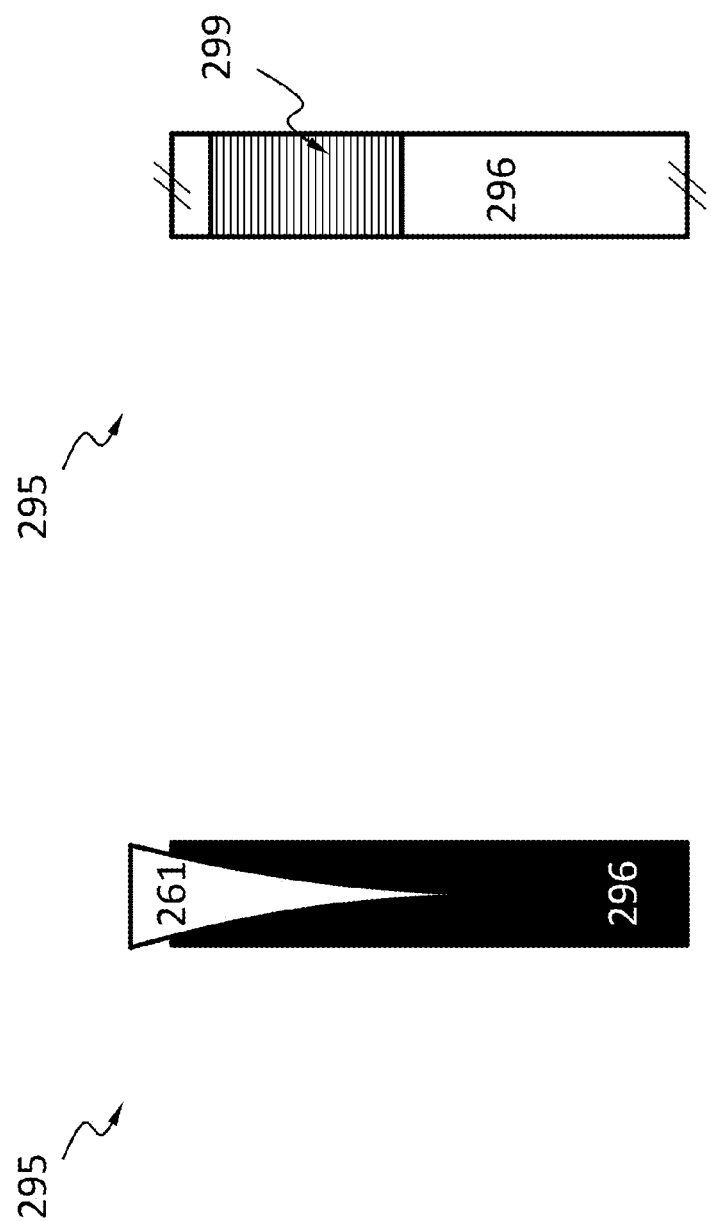

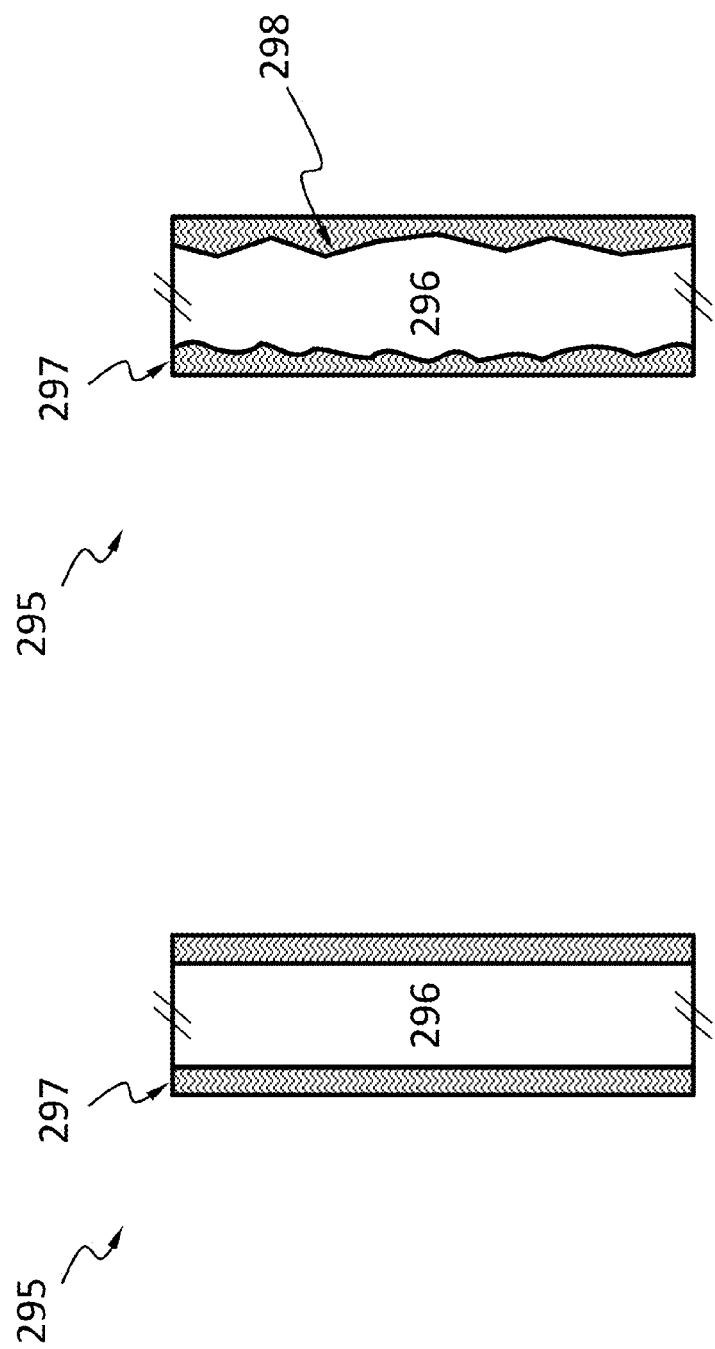

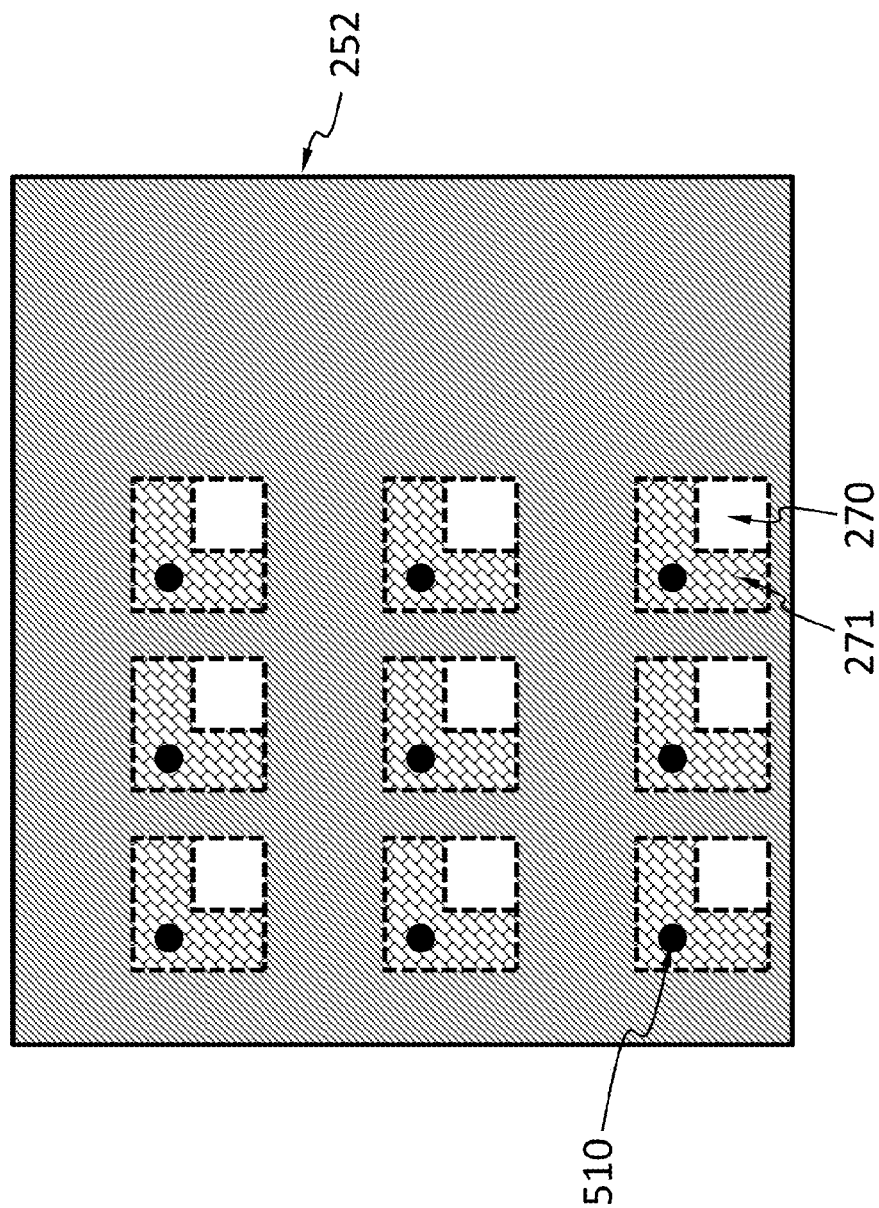

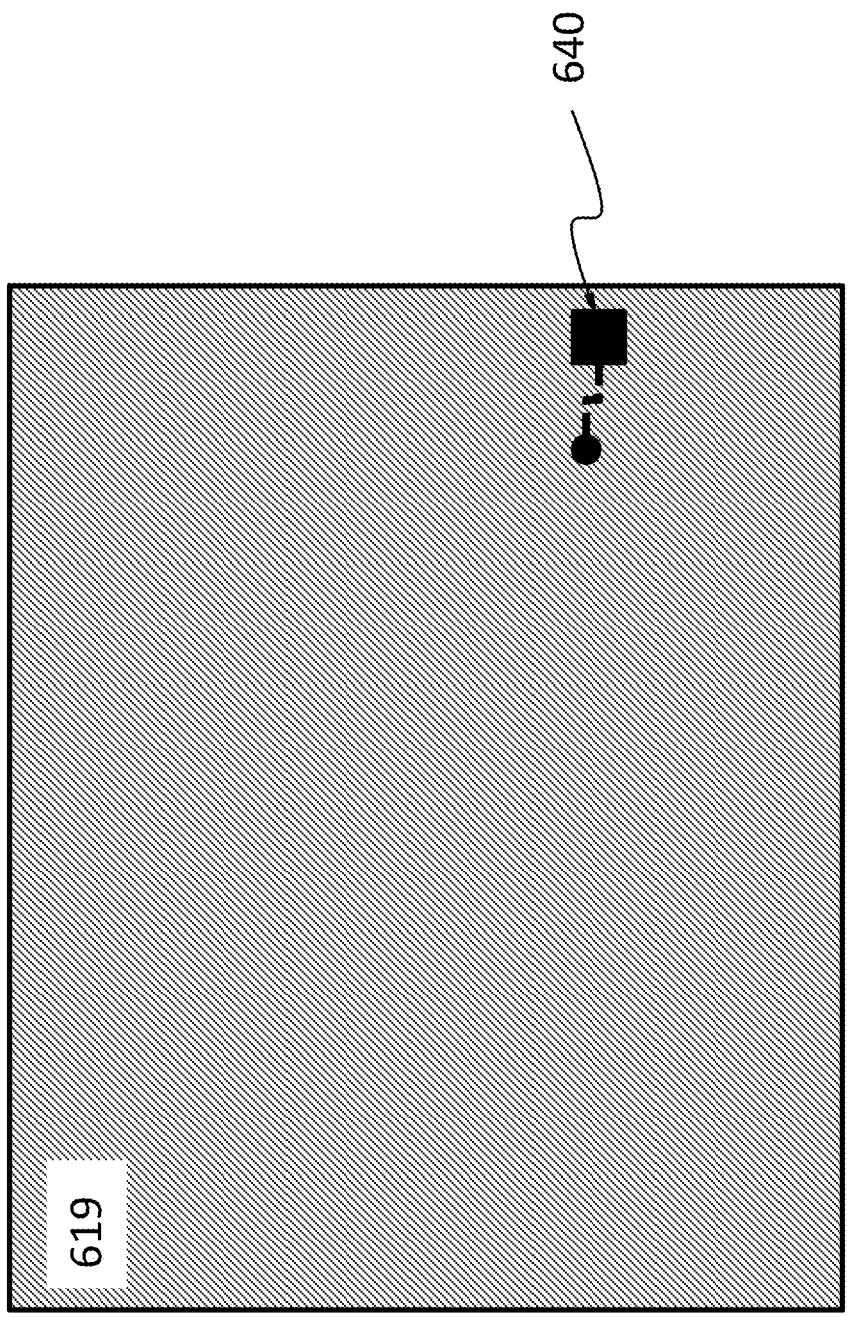

னான்கு
BIOSENSOR

TECHNICAL FIELD

The disclosure herein relates to biosensors, particularly biosensors based on optical detection.

BACKGROUND

A biosensor is an analytical device for detection of an analyte involved in a biological process. For example, the analyte may be a DNA, a protein, a metabolite, or even a living organism (e.g., bacteria, virus).

A biosensor usually has a probe that interacts with the analyte. The probe may be designed to bind or recognize the analyte. Examples of the probe may include antibodies, aptamers, DNAs, RNAs, antigens, etc. Interaction between the probe and the analyte may lead to one or more detectable event. For example, the detectable event may be release of a chemical species or a particle, a chemical reaction, luminescence (e.g., chemiluminescence, bioluminescence, electrochemiluminescence, electroluminescence, photoluminescence, fluorescence, phosphorescence), change in a physical property (e.g., Raman scattering, color) or chemical property (e.g., reactivity, reaction rate).

A biosensor may have a detector that can detect the detectable event as a result of the interaction. The detector may transform the detectable event into another signal (e.g., image, electrical signal) that can be more easily measured and quantified. The detector may include circuitry that obtains data from the detectable event and processes the data.

One type of biosensor is microarray. A microarray can be a two-dimensional array on a solid substrate (e.g., a glass slide, a silicon wafer). The array may have different assays at different locations. The assays at different locations may be independent controlled or measured, thereby allowing multiplexed and parallel sensing of one or many analytes. A microarray may be useful in miniaturizing diagnosis assays. For example, a microarray may be used for detecting biological samples in the fields without sophisticated equipment, or be used by a patient who is not in a clinic or hospital to monitor his or her physiological symptoms.

SUMMARY

Disclosed herein is an apparatus comprising: a plurality of locations configured to have probes attached thereto, wherein interaction between the probes and an analyte generates a signal; an optical system comprising a plurality of collimators; a sensor comprising a plurality of pixels configured to detect the signal; wherein the collimators are configured to essentially prevent light from passing if a deviation of a propagation direction of the light from an optical axis of the collimators is greater than a threshold.

According to an embodiment, the sensor comprises a control circuit configured to control, acquire data from, or process data from the pixels.

According to an embodiment, the pixels are arranged such that each of the pixels is optically coupled to one or more of the locations.

According to an embodiment, the pixels are optically coupled to the locations by the collimators.

According to an embodiment, the signal is luminescence.

According to an embodiment, the signal is generated under excitation of an excitation radiation.

According to an embodiment, the optical system further comprises a filter, wherein the filter is configured to block at least a portion of the excitation radiation.

According to an embodiment, the filter is a dichroic filter.

According to an embodiment, the optical system further comprises or a transmissive layer.

According to an embodiment, the optical system further comprises a plurality of microlens.

According to an embodiment, the threshold is 10°.

According to an embodiment, the collimators comprises a meta-material or a photonic crystal According to an embodiment, the collimators are configured to eliminate optical cross-talk between neighboring pixels among the plurality of pixels.

According to an embodiment, at least one of the collimators comprises a core and a sidewall surrounding the core.

According to an embodiment, the signal is generated under excitation of an excitation radiation; wherein the core is a material that essentially prevents the excitation radiation from passing through irrespective of propagation direction of the excitation radiation.

According to an embodiment, the signal is generated under excitation of an excitation radiation; wherein the core comprises a dichroic filter.

According to an embodiment, the core allows the signal to pass through essentially unabsorbed.

According to an embodiment, the core is a void space.

According to an embodiment, the sidewall attenuates a portion of the signal reaching the sidewall.

According to an embodiment, the sidewall is textured.

According to an embodiment, the apparatus further comprises a redistribution layer configured to route data from the pixels.

According to an embodiment, the filter comprises a meta-material or a photonic crystal.

BRIEF DESCRIPTION OF FIGURES

FIG. 3A schematically shows a collimator, according to an embodiment.

FIG. 3B schematically shows a collimator, according to an embodiment.

FIG. 3C schematically shows a collimator, according to an embodiment.

FIG. 3D schematically shows a collimator, according to an embodiment.

FIG. 5B schematically shows a top view of the sensor in FIG. 5A.

FIG. 6G schematically shows a bottom view of the optical system in FIG. 6A to illustrate the positions of the bonding pad, which are positioned to connect to the via shown in FIG. 6F.

DETAILED DESCRIPTION

Figure 1A:
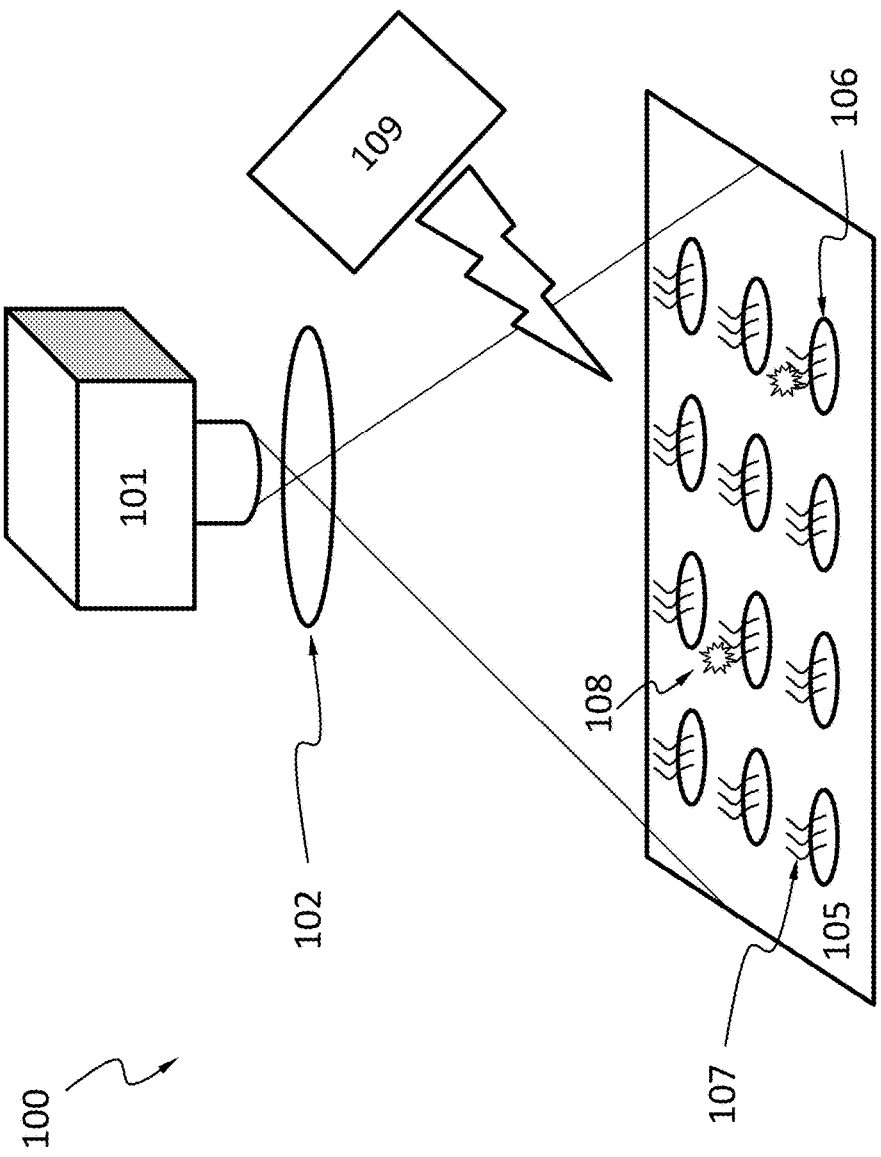
FIG. 1A schematically shows a system including a microarray.

FIG. 1A schematically shows a system 100 including a microarray 105. The system 100 may have an image sensor 101, an optical system 102, and/or an excitation source 109. The image sensor 101 may be configured to measure an optical property (e.g., color, intensity) at different locations 106 of the microarray 105. The locations 106 may have various probes 107 attached thereto. The probes 107 may interact with analyte and the interaction may generate signals 108 detectable by the image sensor 101. The generation of the signals 108 may need excitation by the excitation source 109 (e.g., laser, UV light, etc.). The image sensor 101 and the optical system 102 of the system 100 tend to be bulky, fragile, or expensive and may not have high enough spatial resolution to distinguish one location from its neighboring locations.

Figure 1B:
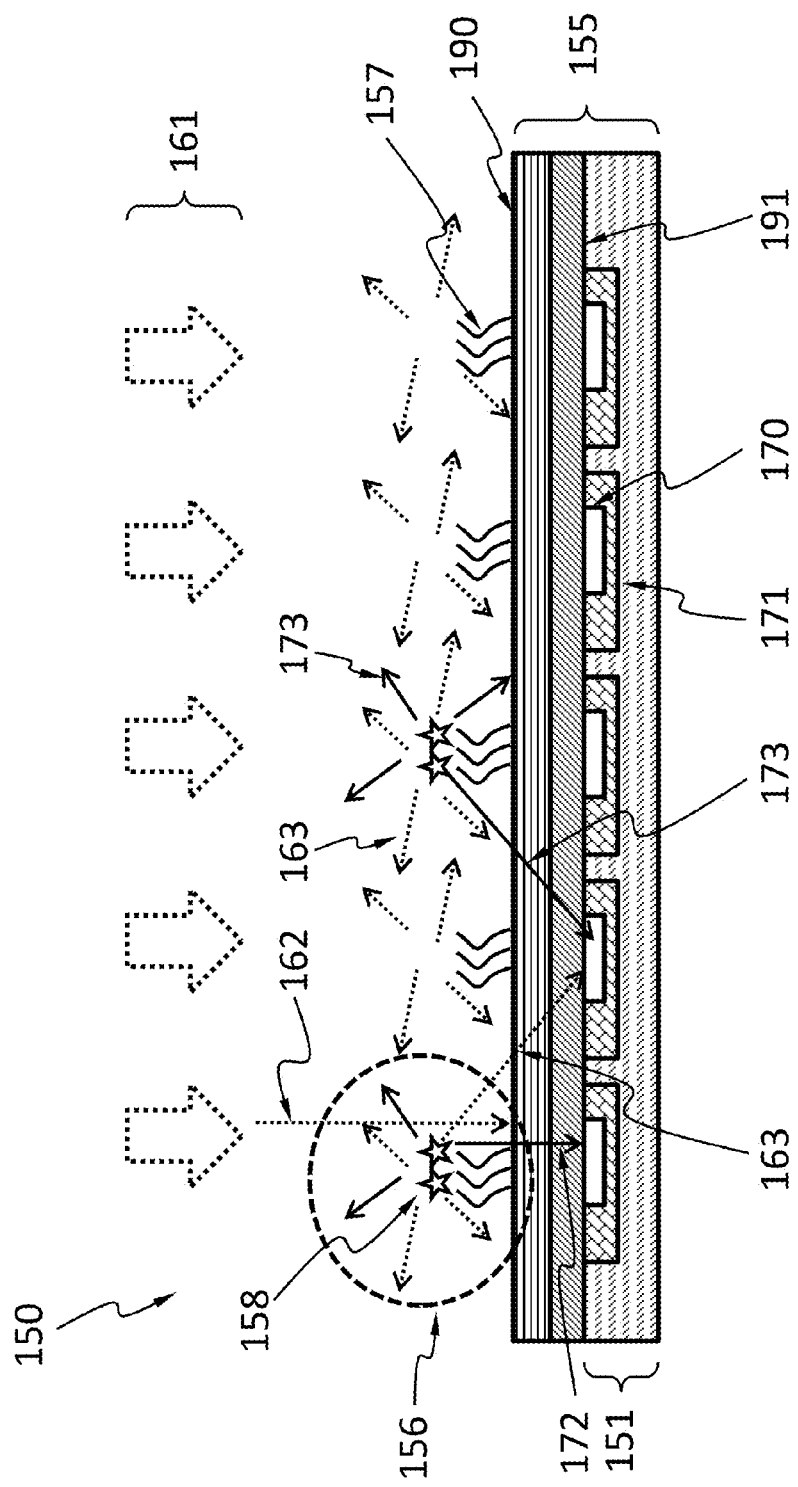
FIG. 1B schematically shows a system where detector capability is integrated into a microarray.

FIG. 1B schematically shows a system 150 where detector capability is integrated into a microarray 155. The microarray 155 may have multiple locations 156 with various probes 157 attached thereto. The probes 157 may interact with various analytes and the interaction may generate signals 158 detectable by a sensor 151 integrated to the microarray 155. For example, the analytes are fluorophore-labeled nucleic acid or protein fragments; the probes are oligonucleotides or antibodies. Locations with fluorophore-labeled analytes captured by the probes can be identified by detecting fluorescence from the fluorophores on the captured analytes. The sensor 151 may have multiple pixels 170 configured to detect the signals 158 (e.g., color, intensity). The pixels 170 may have a control circuit 171 configured to control, acquire data from, and/or process data from the pixels 170. The pixels 170 may be arranged such that each pixel 170 is optically coupled to one of the locations 156. However, the signals 158 generated at one location 156 may not entirely reach the pixel 170 optically coupled to that location 156. A portion 172 of the signals 158 may reach the pixel 170 optically coupled to that location 156 but another portion 173 may be scattered into neighboring pixels ("optical cross-talk") and/or away from all pixels 170. Generating the signals 158 may need an excitation radiation 161 (e.g., laser, UV light, etc.). A portion 162 of the excitation radiation 161 may pass through the locations 156 unscattered. A portion 163 of the excitation radiation 161 may be scattered into some of the pixels 170 or away from all pixels 170. The portion 162 may be blocked by a filter 190 from reaching the pixels 170. The filter 190 may be position below or above a transmissive layer 191. However, the filter 190 may be sensitive to incident directions and may not block the portion 163, despite portions 162 and 163 have the same wavelength. If the portion 163 reaches the pixels 170, it can overshadow signals 158.

Figure 2A:
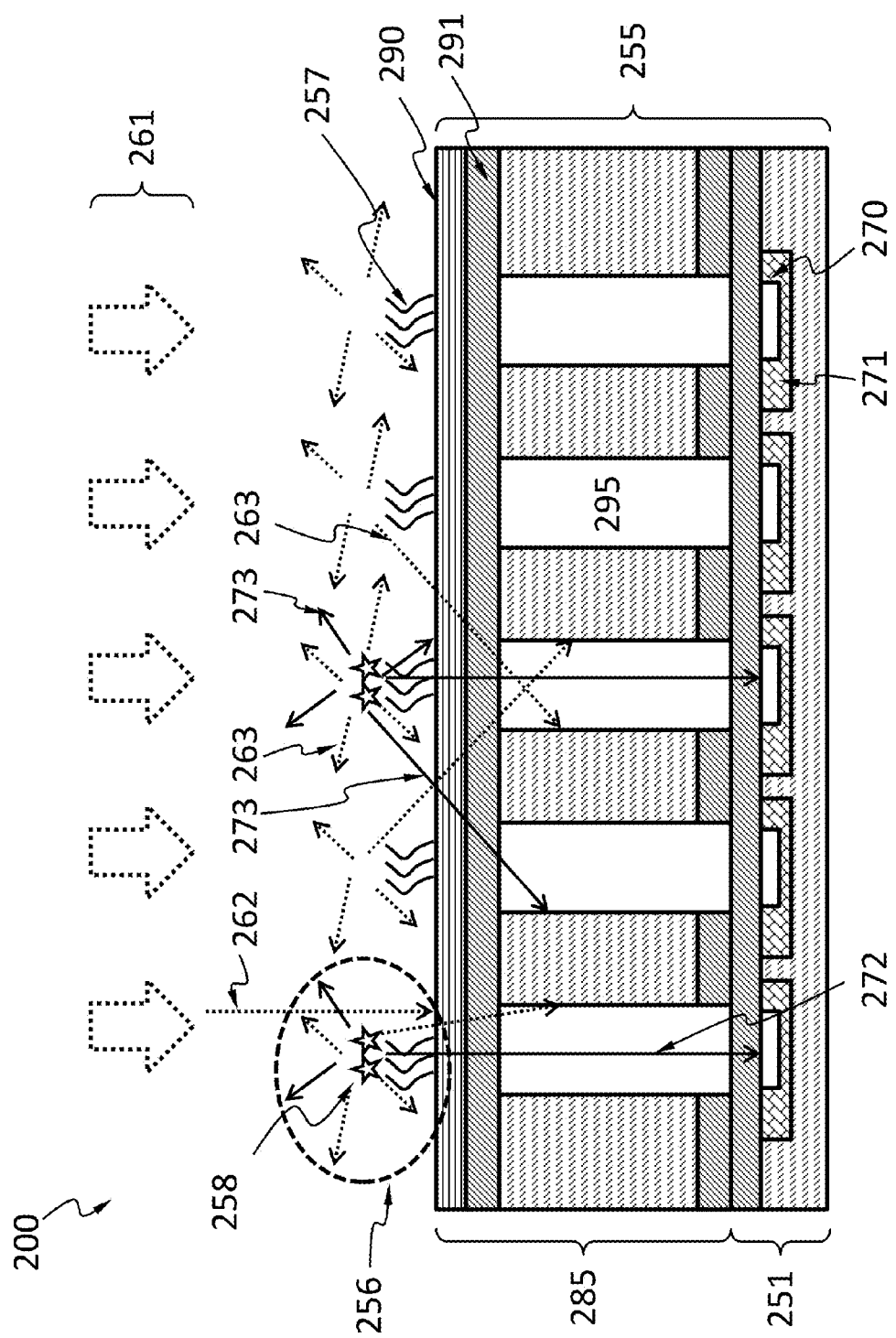
FIG. 2A schematically shows a system, according to an embodiment.
Figure 2B:
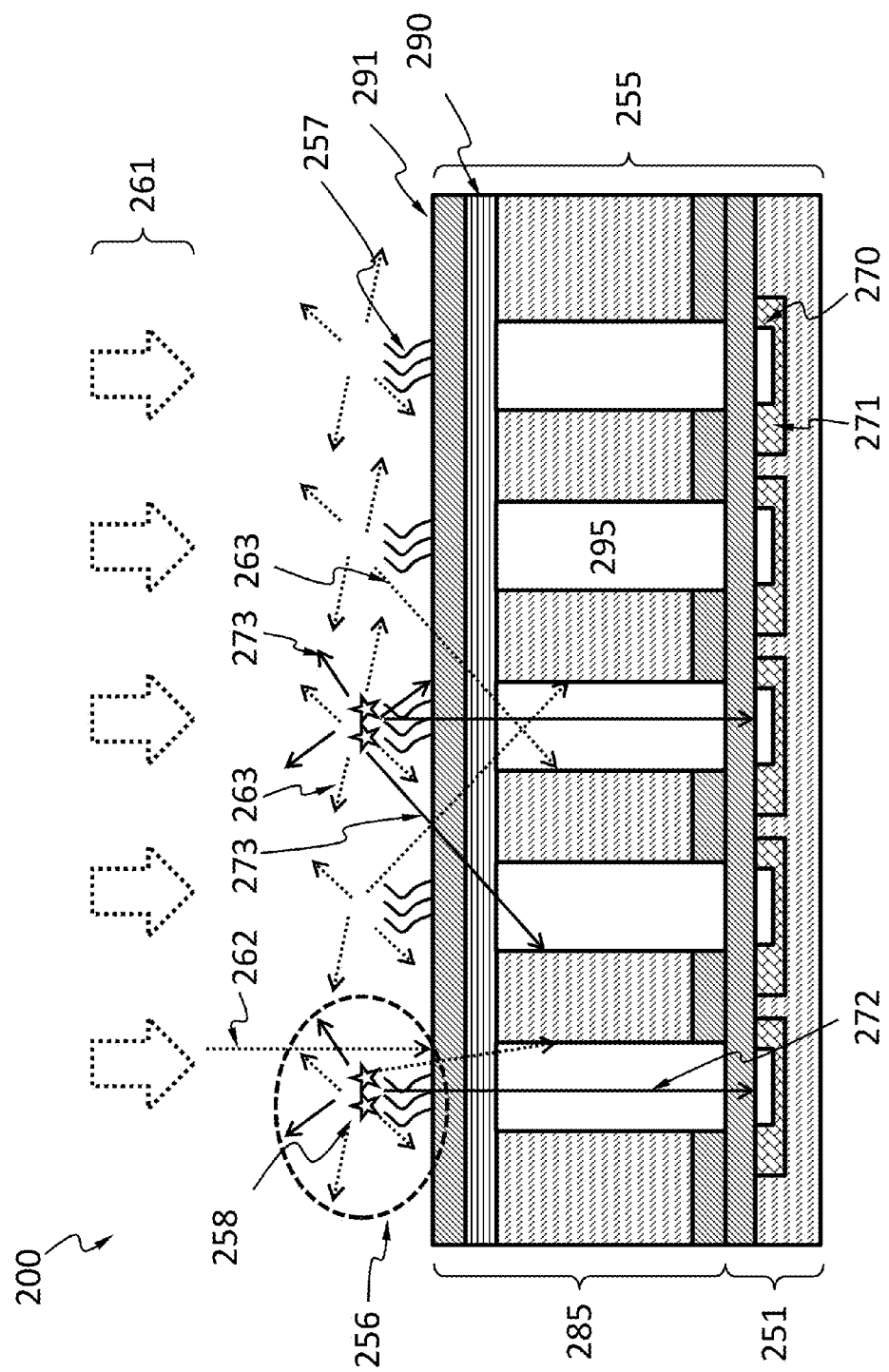
FIG. 2B schematically shows a system, according to an embodiment.

FIG. 2A schematically shows a system 200, according to an embodiment. The system 200 includes a micro array 255 including an integrated sensor 251 and an optical system 285. The microarray 255 may have multiple locations 256 with various probes 257 attached thereto. The probes 257 may interact with various analytes and the interaction may generate signals 258 detectable by the sensor 251. The sensor 251 may have multiple pixels 270 configured to detect the signals 258 (e.g., color, intensity). The pixels 270 may have a control circuit 271 configured to control, acquire data from, and/or process data from the pixels 270. The pixels 270 may be arranged such that each pixel 270 is optically coupled to one or more of the locations 256. The optical system 285 may include a filter 290 positioned below or above a transmissive layer 291 (FIG. 2B shows an example where the filter 290 is below the transmissive layer 291). The optical system 285 may include a plurality of collimators 295 configured to optically couple the pixels 270 to the locations 256. The filter 290 and the transmissive layer 291 may not have to be fabricated on the same substrate as the collimators 295. Instead, the filter 290 and the transmissive layer 291 may be fabricated and bonded to the collimators 295.

In an embodiment, the transmissive layer 291 may include oxide or nitride. For example, the transmissive layer 291 may include glass.

In an embodiment, the filter 290 may be a dichroic filter (also known as interference filter). The filter 290 may be a low-pass (passing frequency below a threshold) or band-pass filter. The filter 290 may include a meta-material or a photonic crystal. A meta-material has component materials arranged in repeating patterns, often at microscopic or smaller scales that are smaller than the wavelengths of the light the meta-material is designed to influence. The structure of the repeated patterns and the properties of the component materials may be selected to tailor the properties of the meta-material. For example, the meta-material may provide optical transparency at all frequencies except at the selected frequency or frequencies which it is configured to block (for example particular laser frequencies that could cause harm to a user). A photonic crystal is a periodic dielectric structure that has a band gap that forbids propagation of a certain frequency range of light. The filter 290 may have multiple thin layers of materials with different refractive indices and may be made by alternately depositing thin layers of these materials. The filter 290 may be an absorptive filter but it would have sufficient thickness to be effective.

Figure 2C:
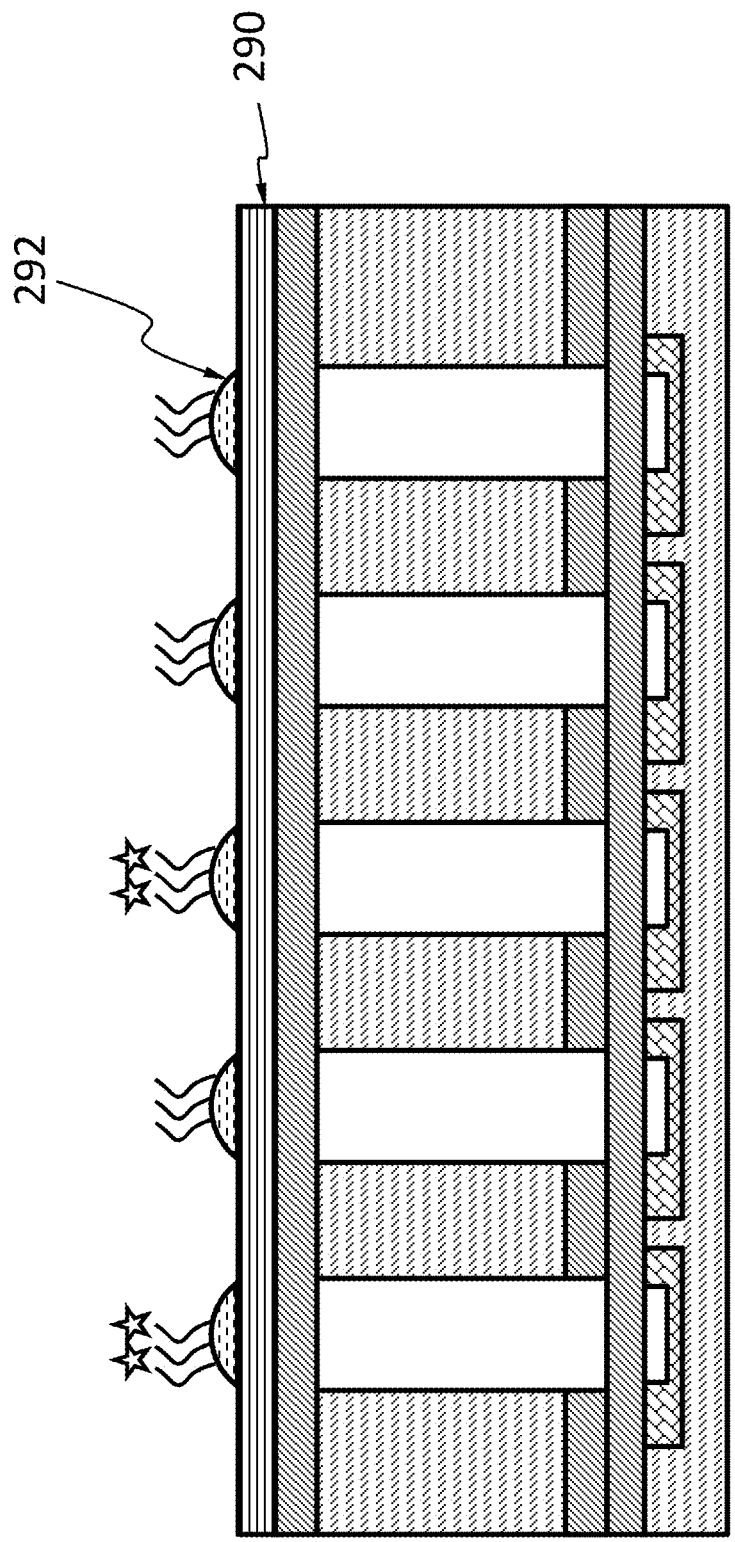
FIG. 2C schematically shows that the system may include microlens, which could be fabricated directly on an exposed surface and the probes may be attached to the microlens, according to an embodiment.
Figure 2D:
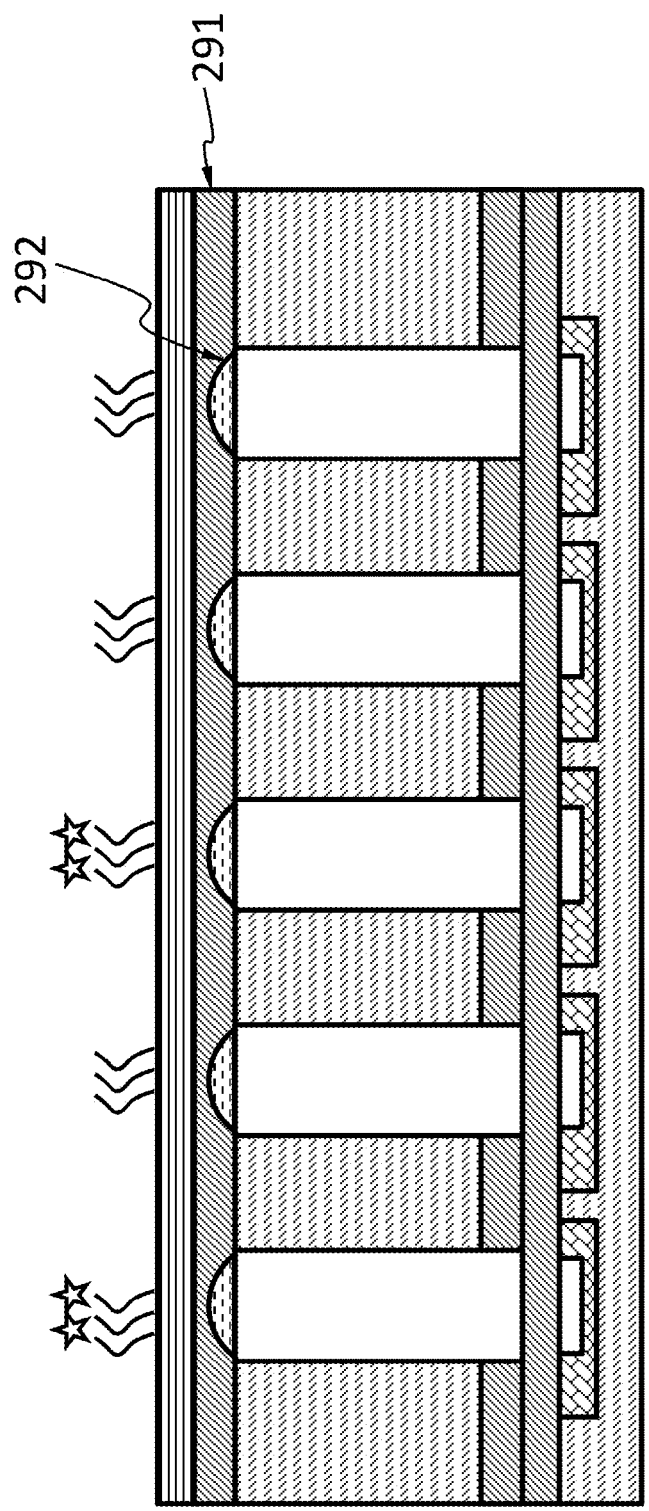
FIG. 2D schematically shows that the microlens may be fabricated in the passivation layer, according to an embodiment.
Figure 2E:
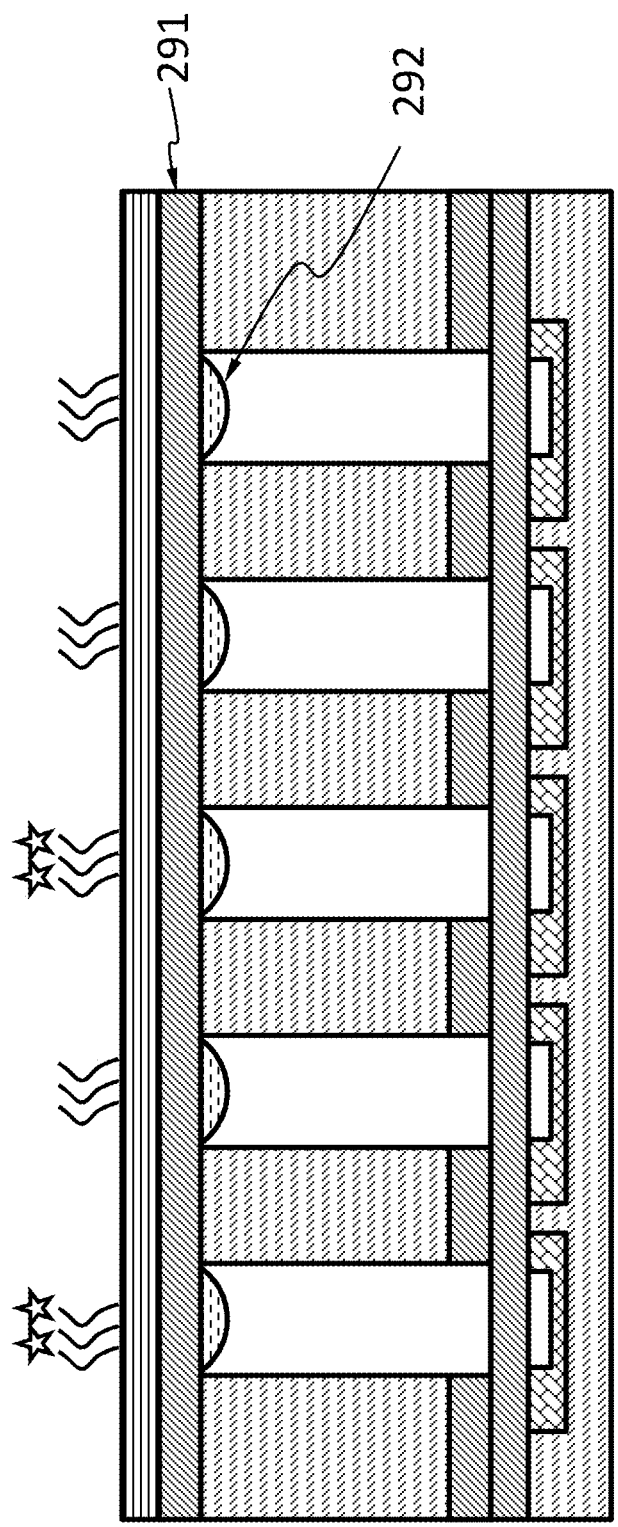
FIG. 2E schematically shows that the microlens may be fabricated in the collimators, according to an embodiment.

In an embodiment, the transmissive layer 291 may be an insulating material such as silicon oxide or silicon nitride. In an embodiment, the transmissive layer 291 may even be omitted. In an embodiment, the optical system 285 may have a plurality of microlens 292 positioned at the locations 256, as shown in FIG. 2C. The microlens 292 may be fabricated directly on an exposed surface of the locations 256 and the probes 257 may be attached to the microlens 292. Alternatively, the microlens 292 may be fabricated in the passivation layer 291 as shown in FIG. 2D. Further alternatively, the microlens 292 may be fabricated in the collimators 295 as shown in FIG. 2E. The microlens 292 may be configured to focus light generated at the locations 256 into the collimators 295. The microlens 292 may be configured to direct a greater portion of luminescence from locations 256 into the pixels coupled thereto. For example, a microlens 292 may capture the portion 273 that otherwise would not reach the pixel coupled to the location 256 where the portion 273 is from.

In an embodiment, the filter 290, the transmissive layer 291 if present, the microlens 292 if present and the collimator 295 may be integrated on the same substrate.

In an embodiment, the collimator 295 may be configured to essentially prevent (e.g., prevent more than 90%, 99%, or 99.9% of) light from passing if the deviation of the propagation direction of the light from an optical axis of the collimator 295 is greater than a threshold (e.g., 10°, 5°, or 1°). A portion 272 of the signals 258 may propagate towards the pixel 270 optically coupled to that location 156 but another portion 273 may be scattered towards neighboring pixels ("optical cross-talk") and/or away from all pixels 270. The collimator 295 may be configured to essentially eliminate optical cross-talk by essentially preventing the portion 273 from passing through the collimator 295. Generating the signals 258 may need an excitation radiation 261 (e.g., laser, UV light, etc.). A portion 262 of the excitation radiation 261 may pass through the locations 256 unscattered. A portion 263 of the excitation radiation 261 may be scattered into other directions towards some of the pixels 270 or away from all pixels 270. The portion 262 may be blocked by the filter 290 from reaching the pixels 270. The filter 290 may be sensitive to incident directions and may not block the portion 263, despite portions 262 and 263 have the same wavelength. The collimators 295 may be configured to essentially prevent the excitation radiation from passing through irrespective of the propagation direction, or to essentially prevent the portion 263 scattered away from the propagation direction of the portion 261 from passing through.

In an embodiment, each of the collimators 295 extends from one of the locations 256 to the pixel 270 optically coupled to that one location.

In an embodiment, the collimator 295 may have a core 296 surrounded by a sidewall 297.

In an embodiment schematically shown in FIG. 3A, the core 296 may be a material that essentially prevents (e.g., prevents more than 90%, 99%, or 99.9% of) the excitation radiation 261 from passing through irrespective of the propagation direction of the excitation radiation 261. For example, the core 296 may be a material that attenuates (absorbs) the excitation radiation 261. The core 296 may allow the signals 258 to pass through essentially unabsorbed. In this embodiment, the filter 290 may be omitted.

In an embodiment schematically shown in FIG. 3B, the core 296 may have a structure 299 that essentially prevents (e.g., prevents more than 90%, 99%, or 99.9% of) a portion of the excitation radiation 261 from passing through if the deviation of the propagation direction of the portion (e.g., portion 272) from the optical axis of the collimator 295 is smaller than a threshold (e.g., 10°, 5°, or 1°). For example, the structure 299 may have a dichroic filter, a meta-material or a photonic crystal. The core 296 may allow the signals 258 to pass through essentially unabsorbed (i.e., less than 10% absorbed). In this embodiment, the filter 290 may be omitted.

In an embodiment, schematically shown in FIG. 3C, the sidewall 297 of the collimator 295 may attenuate (absorb) the excitation radiation. The portion 263 of the excitation radiation 261 may pass through the filter 290 and enter the collimator 295 but is likely to reach the sidewall 297 before it can reach the pixels 270. The sidewall 297 that can attenuate (absorb) the excitation radiation will essentially prevent stray excitation radiation from reaching the pixels 270. In an embodiment, the core 296 may be a void space. Namely, the sidewall 297 surrounds a void space.

In an embodiment, the sidewall 297 may attenuate (absorb) any portion of the signal 258 reaching the sidewall, which will essentially prevent optical cross-talk.

In an embodiment, schematically shown in FIG. 3D, the sidewall 297 is textured. For example, the interface 298 between the sidewall 297 and the core 296 (which can be a void space) may be textured. Textured sidewall 297 can help further attenuate light incident thereon.

Figure 3E:
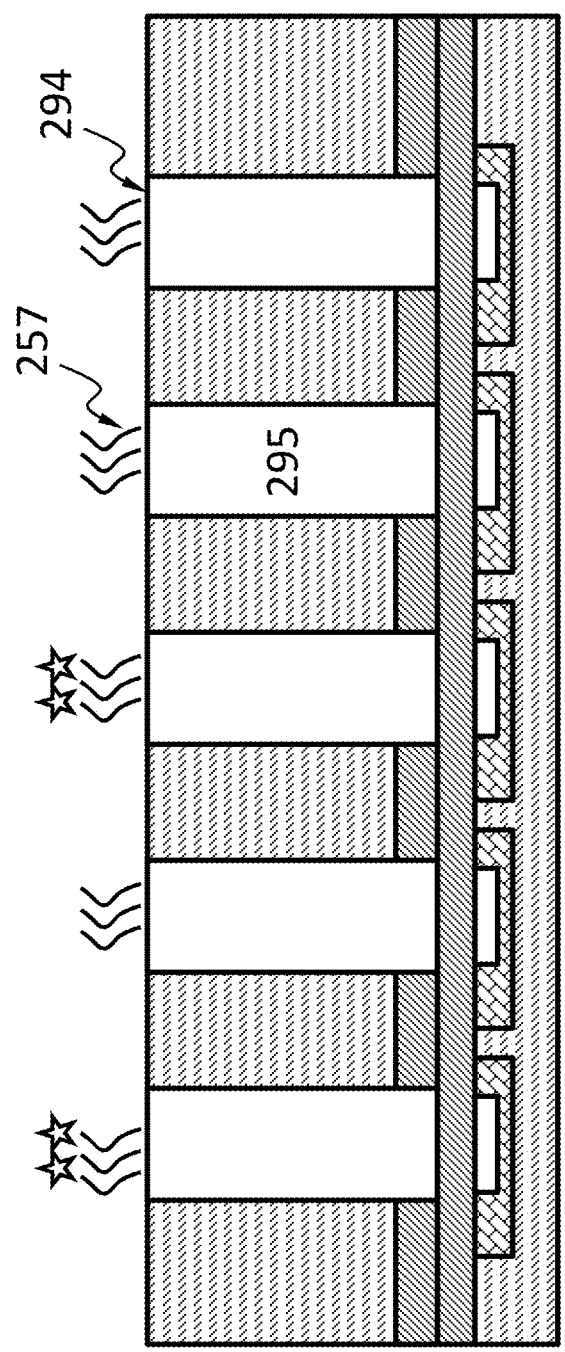
FIG. 3E schematically shows a system where the filter and the transmissive layer are both omitted, according to an embodiment.

In an embodiment, schematically shown in FIG. 3E, the filter 290 and the transmissive layer 291 may be both omitted. The collimator 295 may have a top surface 294 exposed. The top surface 294 may be of a different material from its neighboring surface, thereby facilitating functionalization of the top surface 294. The probes 257 may be selectively attached directly to the top surface 294.

Figure 3F:
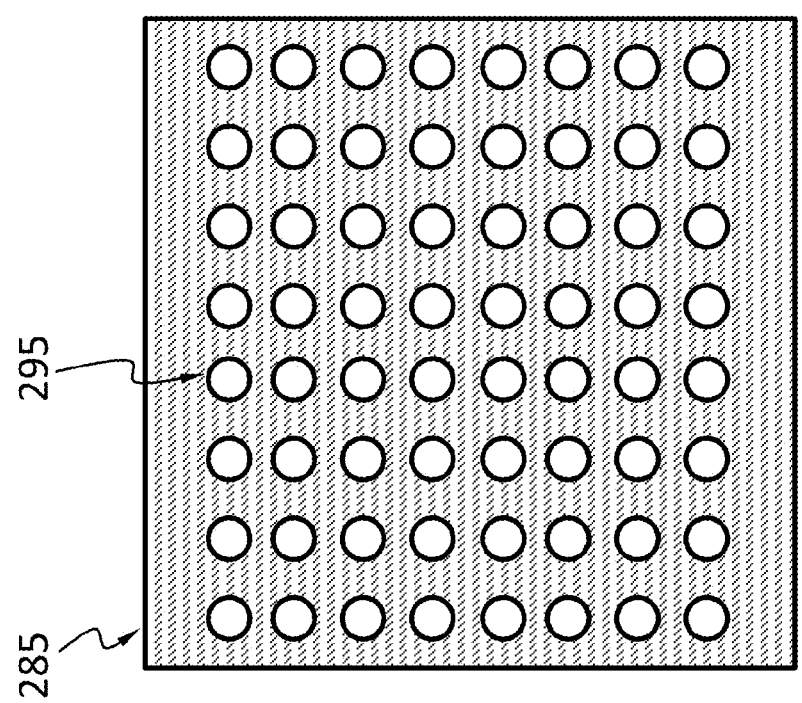
FIG. 3F and FIG. 3G each schematically show that the optical system may have a plurality of collimators arranged in an array, according to an embodiment.
Figure 3G:
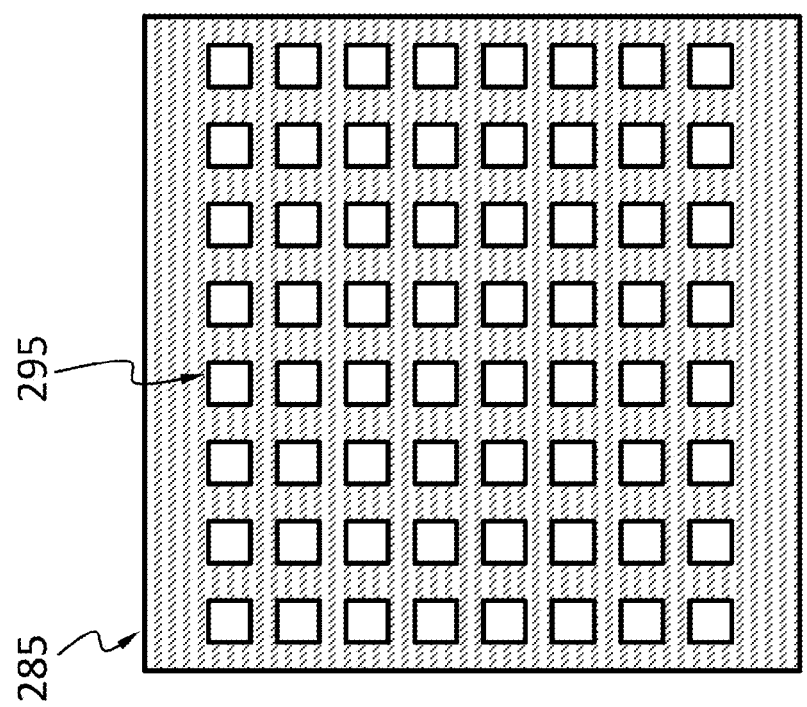

In an embodiment, schematically shown in FIG. 3F and FIG. 3G, the optical system 285 may have a plurality of collimators 295 arranged in an array. For example, the optical system 285 may have a dedicated collimator 295 for each pixel 270. For example, the optical system 285 may have a collimator 295 shared by a group of pixels 270. The collimator 295 may have any suitable cross-sectional shape, such as circular, rectangular, and polygonal.

In an embodiment, the collimators 295 may be made by etching (by e.g., deep reactive ion etching (deep RIE), laser drilling) holes into a substrate. The sidewall 297 may be made by depositing a material on the sidewall of the holes. The core 296 may be made by filling the holes. Planarization may also be used in the fabrication of the collimators 295.

In an embodiment, the filter 290 may be omitted or its function may be integrated into the collimators 295.

Figure 4:
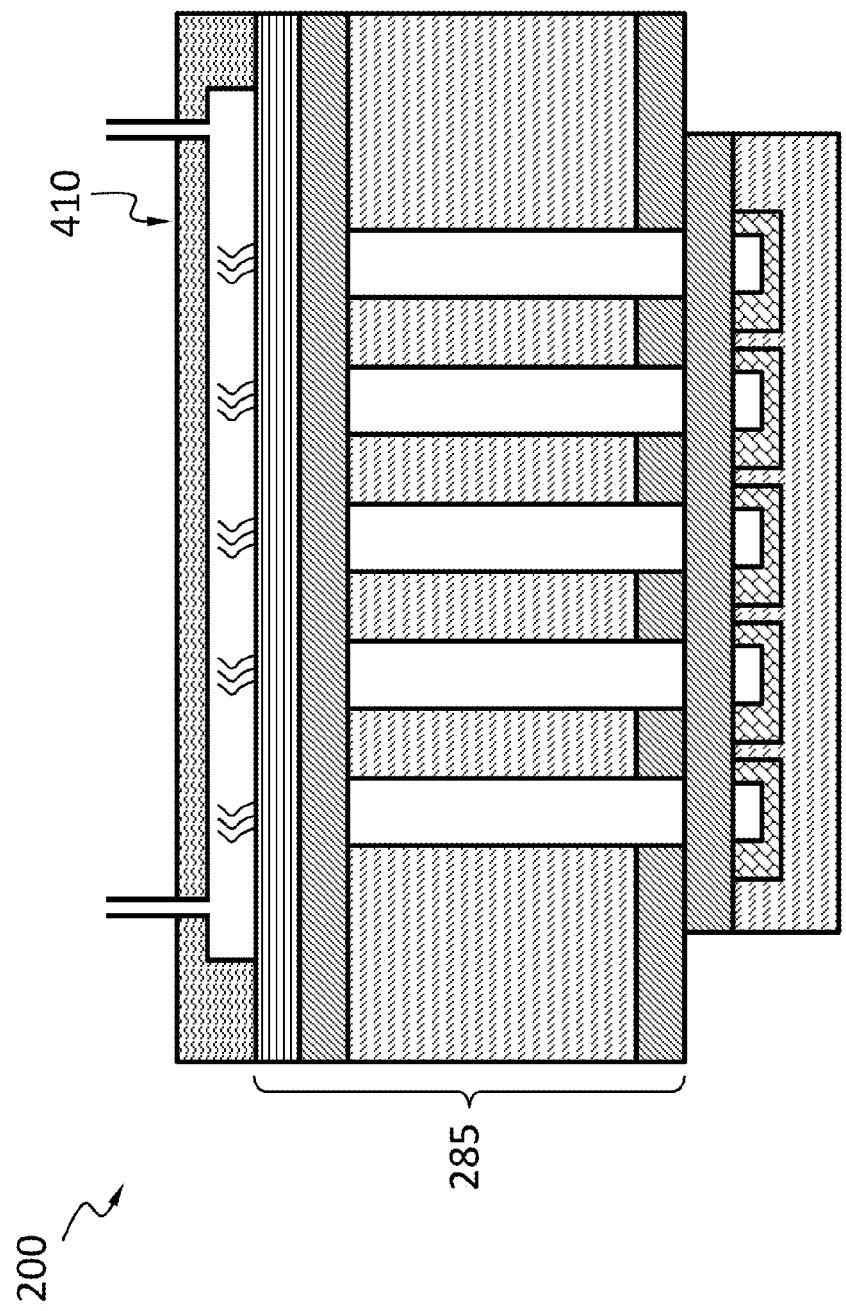
FIG. 4 schematically shows that the optical system may have a microfluidic system, according to an embodiment.

In an embodiment, schematically in FIG. 4, the optical system 285 may have a microfluidic system to deliver reactants such as the analyte and reaction product to and from the locations 256. The microfluidic system may have wells, reservoirs, channels, valves or other components. The microfluidic system may also have heaters, coolers (e.g., Peltier devices), or temperature sensors. The heaters, coolers or temperature sensors may be located in the optical system 285, above or in the collimators 295. The heaters, coolers or temperature sensors may be located above or in the sensor 251. The system 200 may be used for a variety of assays. For example, the system 200 can be used to conduct real-time polymerase chain reaction (e.g., quantitative real-time PCR (qPCR)). Real-time polymerase chain reaction (real-time PCR) detects amplified DNA as the reaction progresses. This is in contrast to traditional PCR where the product of the reaction is detected at the end. One real-time PCR technique uses sequence-specific probes labelled with a fluorophore which fluoresces only after hybridization of the probe with its complementary sequence, which can be used to quantify messenger RNA (mRNA) and non-coding RNA in cells or tissues.

The optical system 285 and the sensor 251 may be fabricated in separate substrates and bonded together using a suitable technique, such as, flip-chip bonding, wafer-to-wafer direct bonding, or gluing.

Figure 5A:
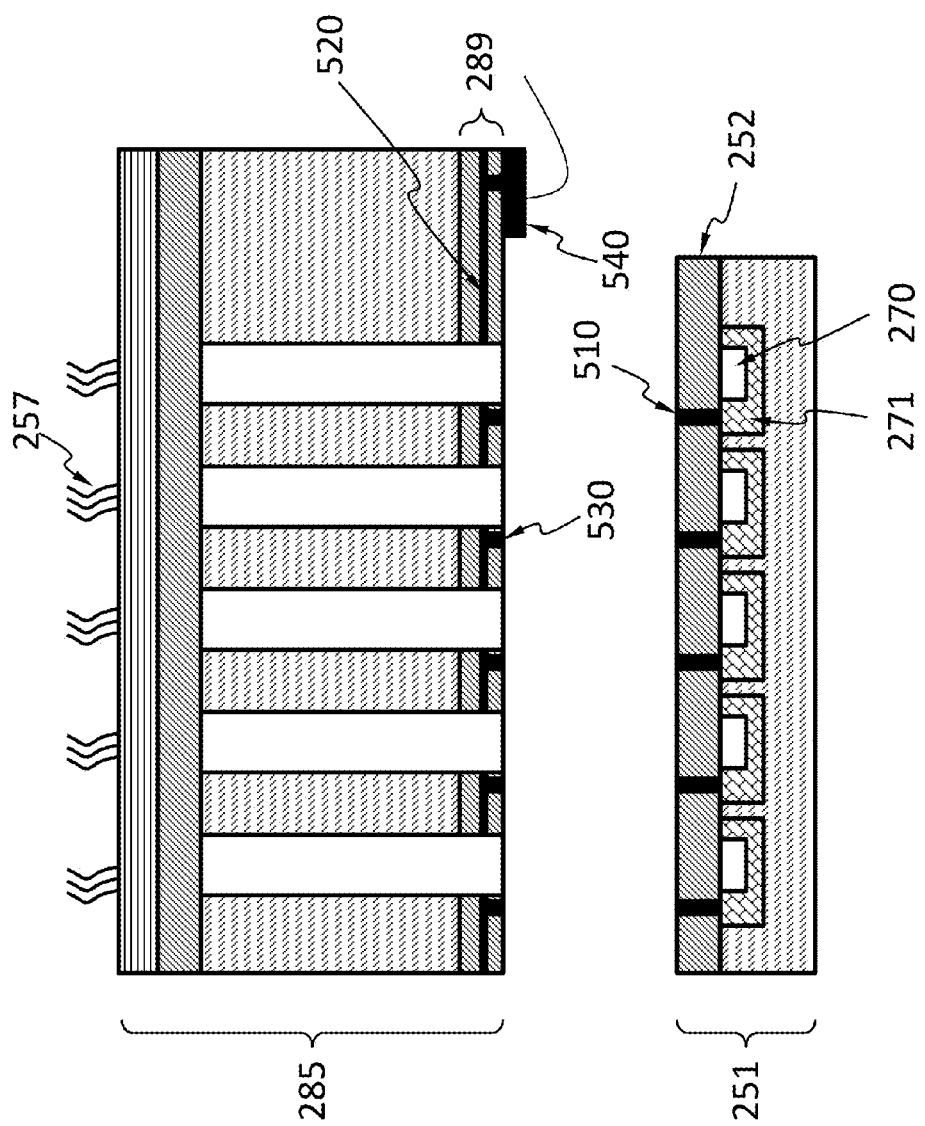
FIG. 5A schematically shows that a sensor in a microarray may have a signal transfer layer and that the optical system in the microarray may have a redistribution layer, according to an embodiment.

In an embodiment, schematically shown in FIG. 5A, the sensor 251 has a signal transfer layer 252. The signal transfer layer 252 may have a plurality of vias 510. The signal transfer layer 252 may have electrically insulation materials (e.g., silicon oxide) around the vias 510. The optical system 285 may have a redistribution layer 289 with transmission lines 520 and vias 530. The transmission lines 520 connect the vias 530 to bonding pads 540. When the sensor 251 and the optical system 285 are bonded, the vias 510 and the vias 530 are electrically connected. This configuration shown in FIG. 5A allows the bonding pads 540 to be positioned away from the probes 257.

Figure 5C:
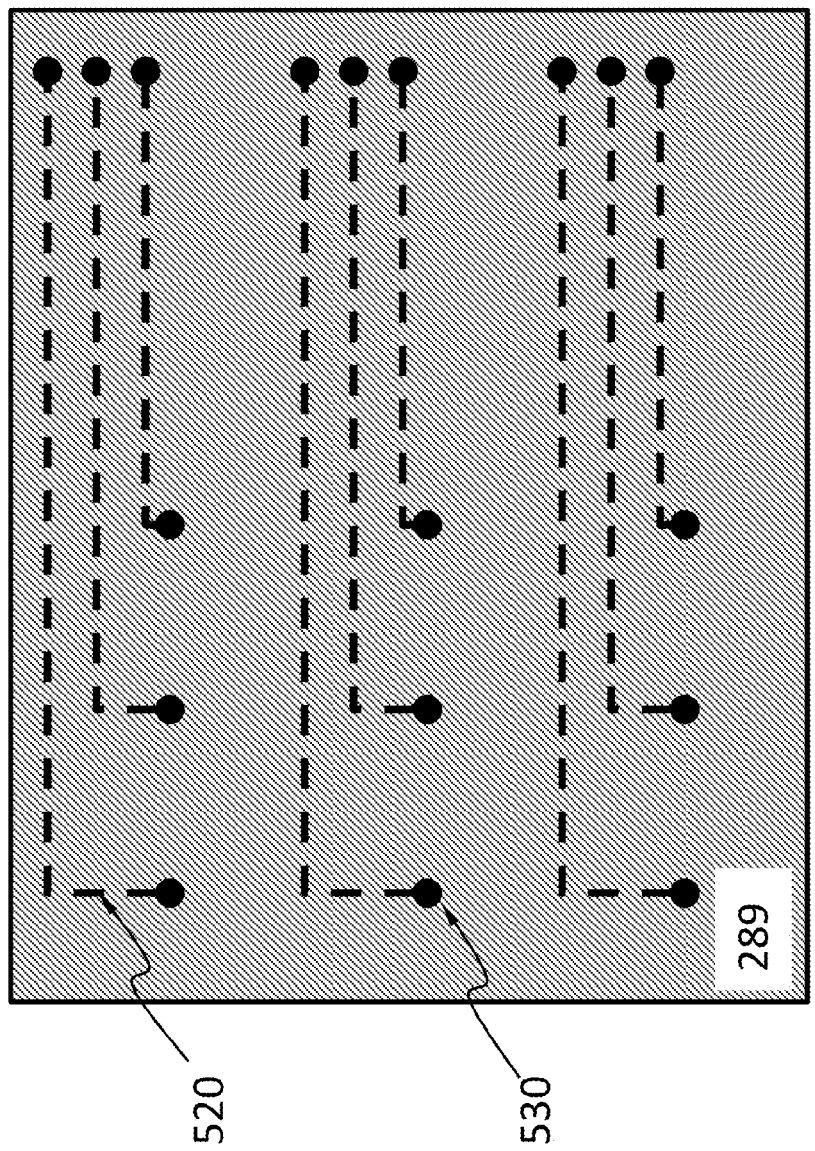
FIG. 5C schematically shows a bottom view of the optical system in FIG. 5A.

FIG. 5B shows a top view of the sensor 251 in FIG. 5A to illustrate the positions of the vias 510 relative to the pixels 270 and the control circuit 271. The pixels 270 and the control circuit 271 are shown in dotted lines because they are not directly visible in this view. FIG. 5C shows a bottom view of the optical system 285 in FIG. 5A to illustrate the positions of the vias 530 relative to the transmission lines 520 (shown as dotted lines because they are not directly visible in this view).

Figure 6A:
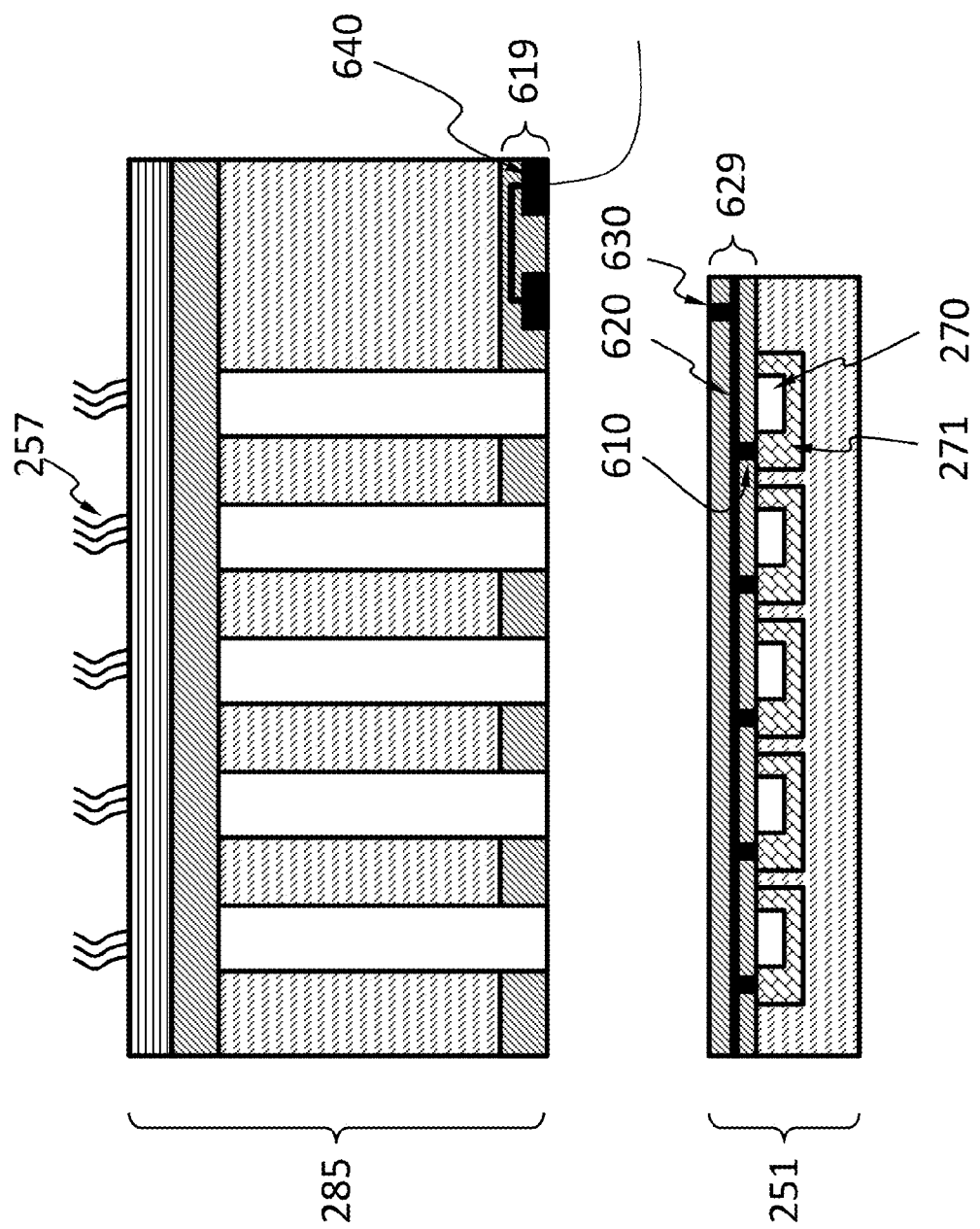
FIG. 6A schematically shows that a sensor in a microarray may have a redistribution layer and that the optical system in the microarray may have a signal transfer layer, according to an embodiment.

In an embodiment, schematically shown in FIG. 6A, the sensor 251 has a redistribution layer 629. The redistribution layer 629 may have a plurality of vias 610 and a plurality of transmission lines 620. The redistribution layer 629 may have electrically insulation materials (e.g., silicon oxide) around the vias 610 and the transmission lines 620. The vias 610 electrically connect the control circuit 271 to the transmission lines 620. The optical system 285 may have a layer 619 with bonding pads 640. The redistribution layer 629 may also have vias 630 electrically connecting the transmission lines 620 to the bonding pads 640, when the sensor 251 and the optical system 285 are bonded. The bonding pads 640 may have two parts connected by a wire buried in the layer 619. This configuration shown in FIG. 6A allows the bonding pads 640 to be positioned away from the probes 257.

Figure 6B:
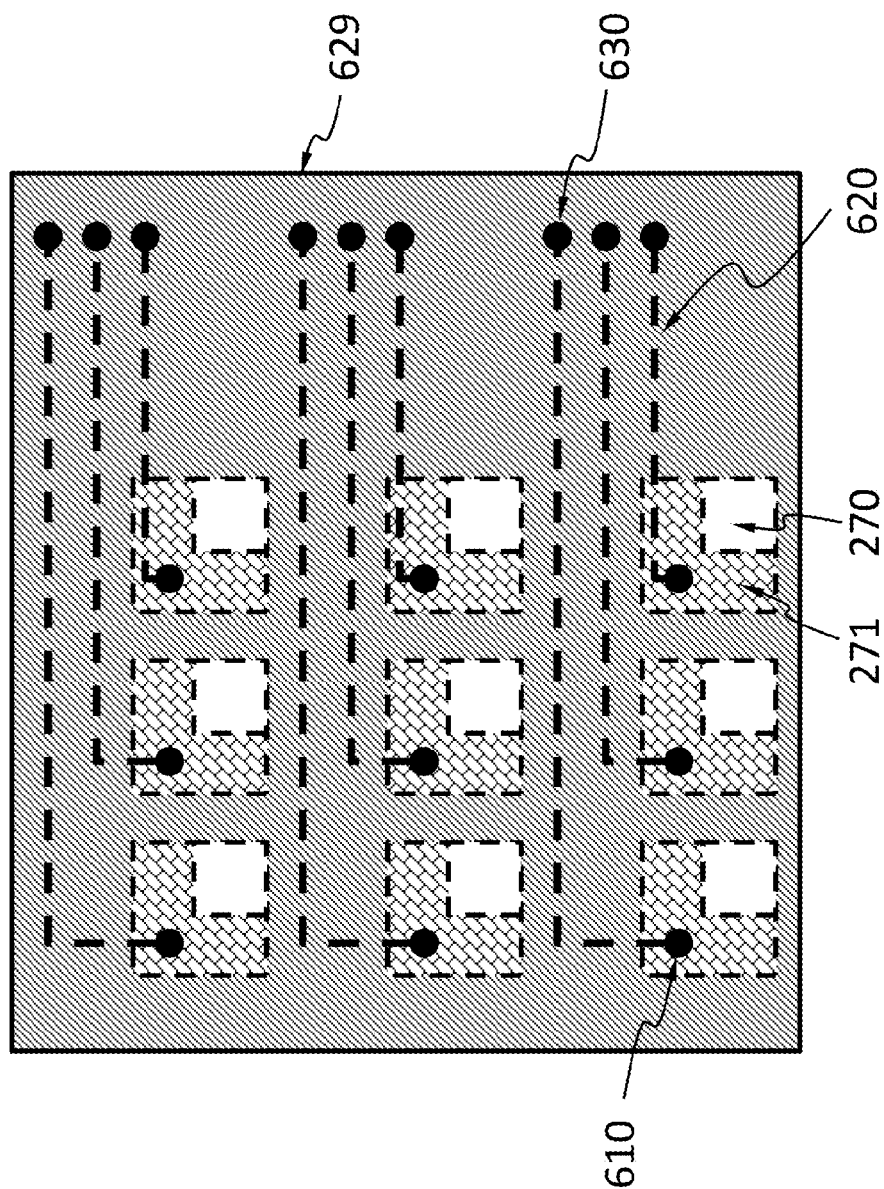
FIG. 6B schematically shows a top view of the sensor in FIG. 6A, according to an embodiment.
Figure 6C:
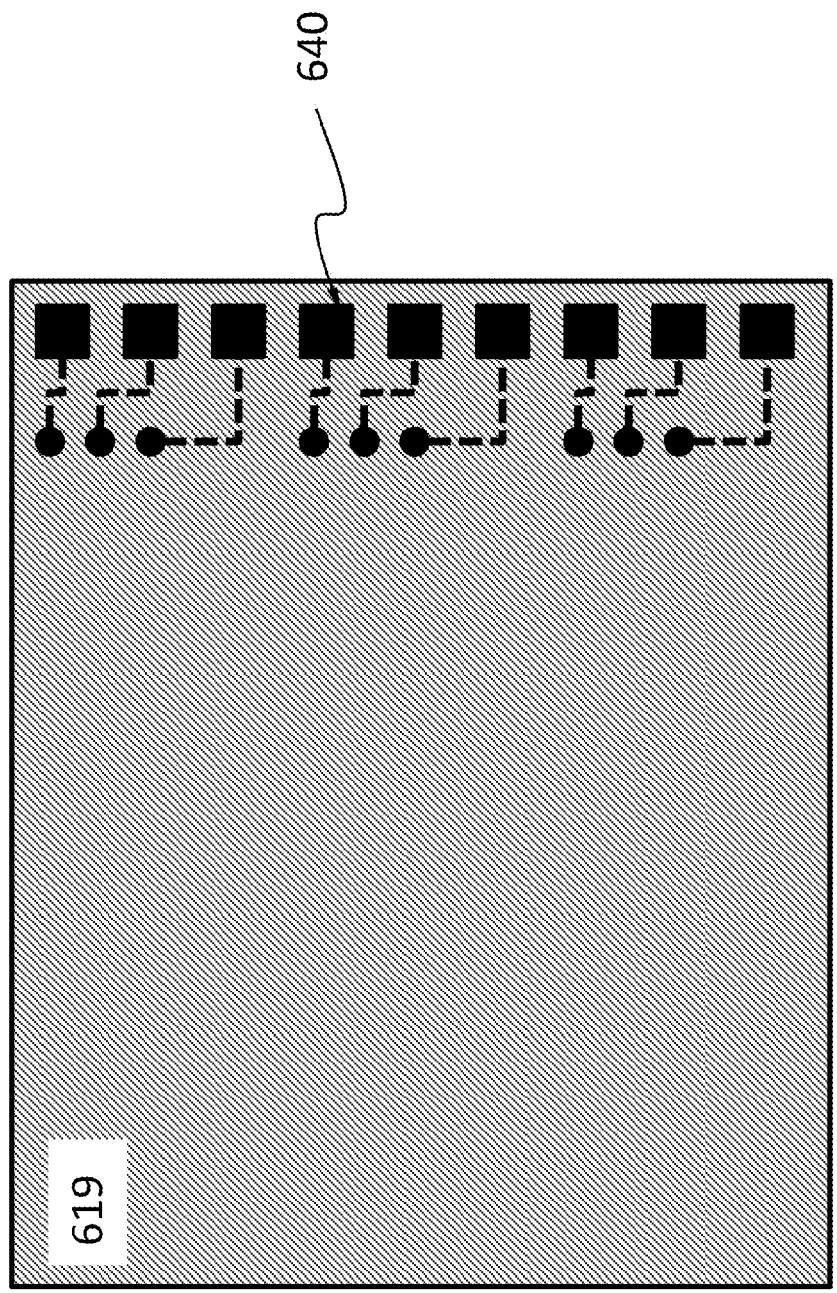
FIG. 6C schematically shows a bottom view of the optical system in FIG. 6A, according to an embodiment.

FIG. 6B shows a top view of the sensor 251 in FIG. 6A to illustrate the positions of the vias 610, the vias 630 and the transmission lines 620, relative to the pixels 270 and the control circuit 271, according to an embodiment. The pixels 270, the control circuit 271 and the transmission lines 620 are shown in dotted lines because they are not directly visible in this view. FIG. 6C shows a bottom view of the optical system 285 in FIG. 6A to illustrate the positions of the bonding pads 640, which are positioned to connect to the vias 630 shown in FIG. 6B. The bonding pads 640 may have two parts connected by a wire buried in the layer 619.

Figure 6D:
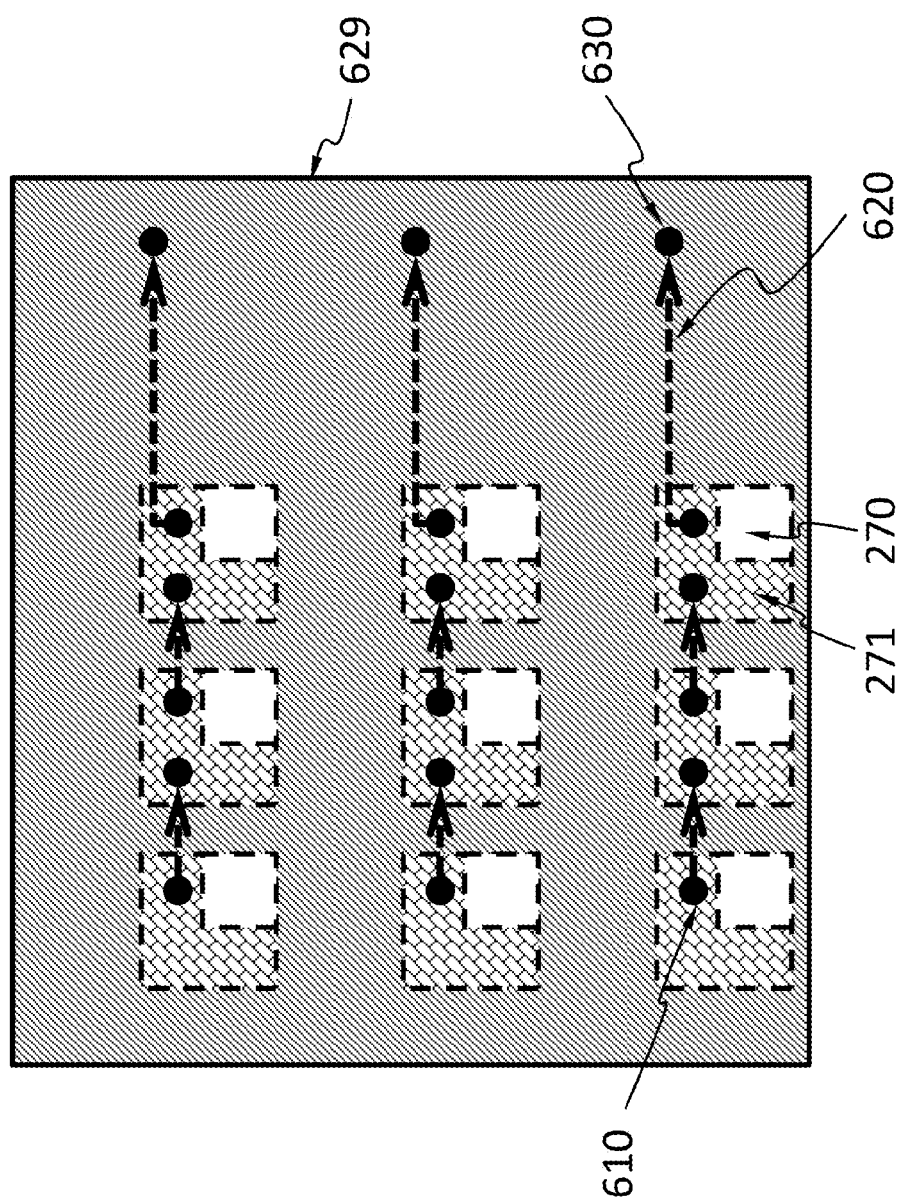
FIG. 6D schematically shows a top view of the sensor in FIG. 6A, according to an embodiment.
Figure 6E:
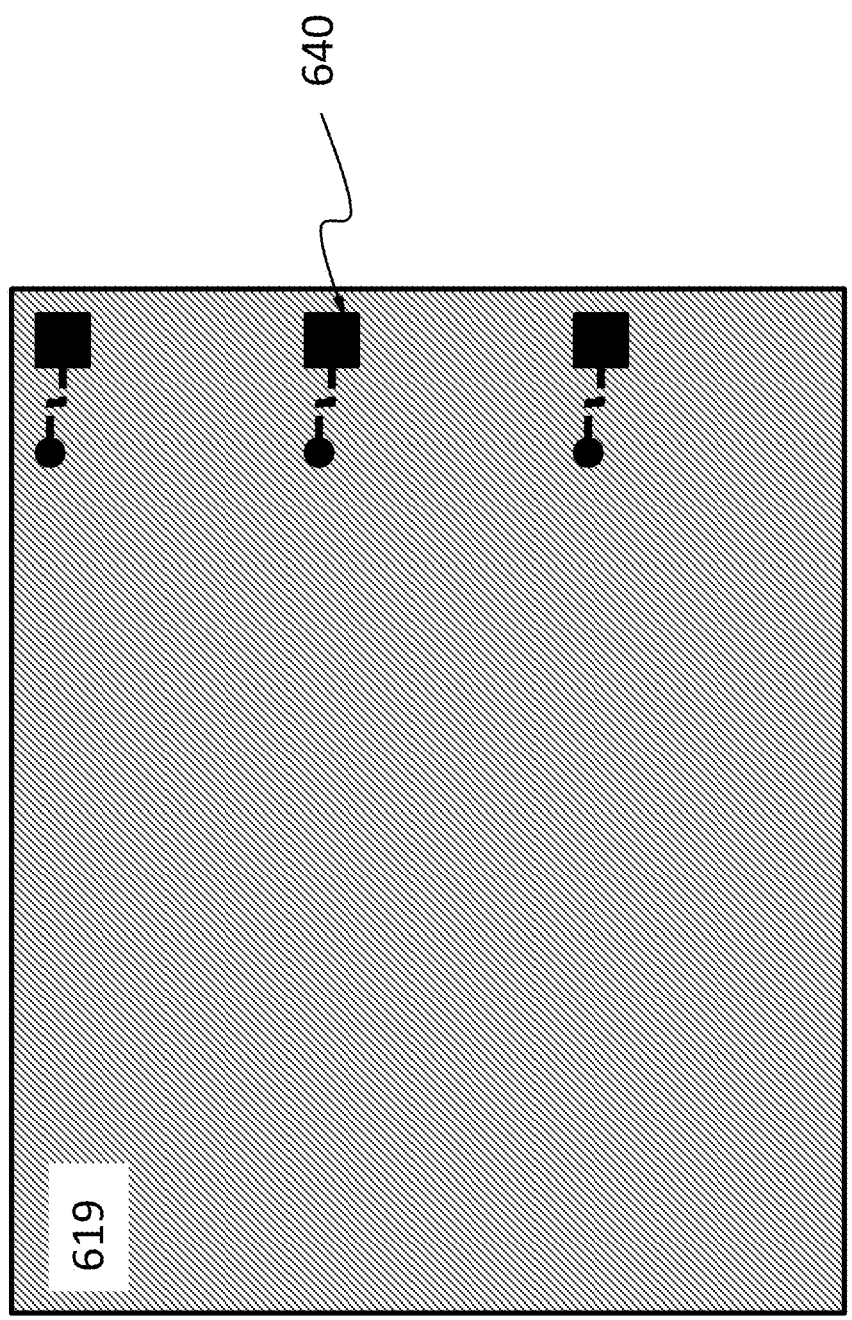
FIG. 6E schematically shows a bottom view of the optical system in FIG. 6A to illustrate the positions of the bonding pads, which are positioned to connect to the vias shown in FIG. 6D.

FIG. 6D shows a top view of the sensor 251 in FIG. 6A to illustrate the positions of the vias 610, the vias 630 and the transmission lines 620, relative to the pixels 270 and the control circuit 271, according to an embodiment. The pixels 270, the control circuit 271 and the transmission lines 620 are shown in dotted lines because they are not directly visible in this view. The pixels 270 may be read out column by column. For example, signal from one 270 may be stored in register in the control circuit 271 associated with that pixel 270; the signal may be successively shifted from one column to the next, and eventually to other processing circuitry through vias 630. FIG. 6E shows a bottom view of the optical system 285 in FIG. 6A to illustrate the positions of the bonding pads 640, which are positioned to connect to the vias 630 shown in FIG. 6D. The bonding pads 640 may have two parts connected by a wire buried in the layer 619.

Figure 6F:
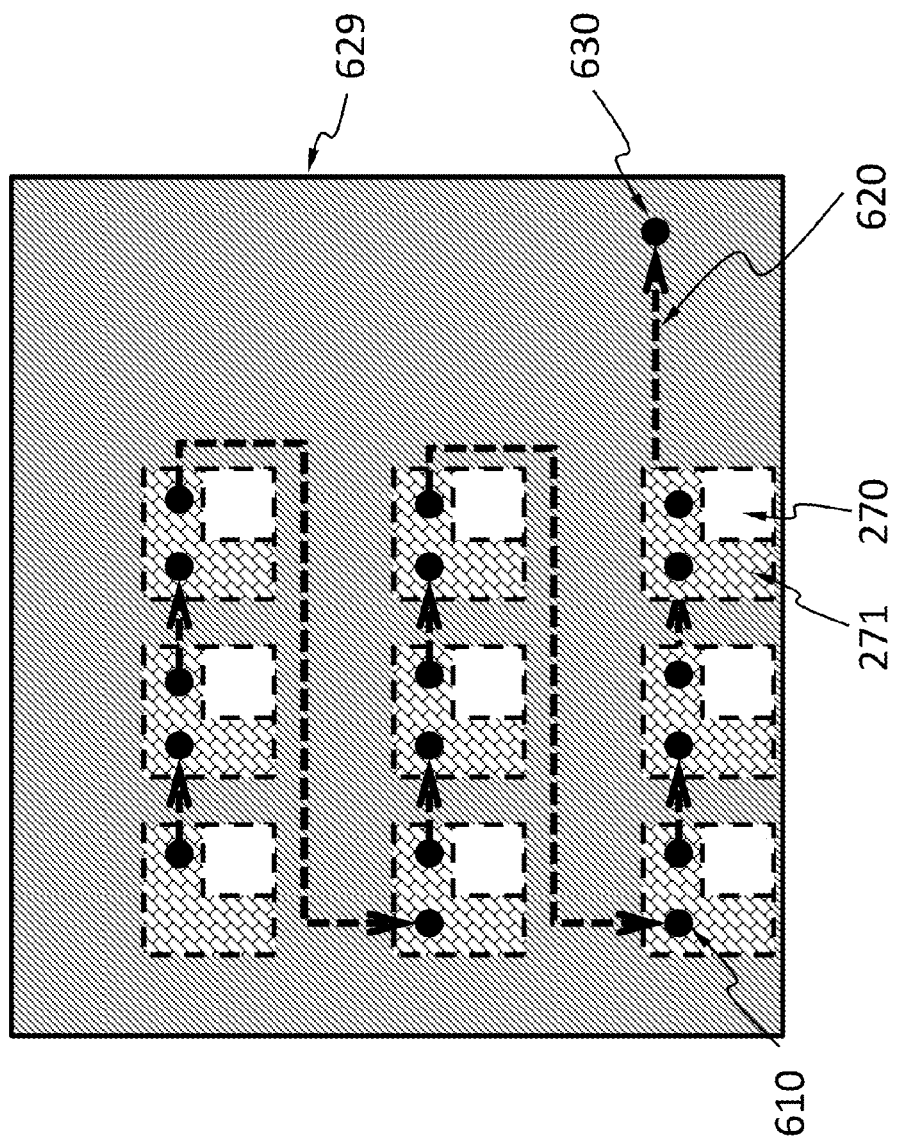
FIG. 6F schematically shows a top view of the sensor in FIG. 6A, according to an embodiment.

FIG. 6F shows a top view of the sensor 251 in FIG. 6A to illustrate the positions of the vias 610, the via 630 and the transmission lines 620, relative to the pixels 270 and the control circuit 271, according to an embodiment. The pixels 270, the control circuit 271 and the transmission lines 620 are shown in dotted lines because they are not directly visible in this view. The pixels 270 may be read out pixel by pixel. For example, signal from one 270 may be stored in register in the control circuit 271 associated with that pixel 270; the signal may be successively shifted from one pixel to the next, and eventually to other processing circuitry through via 630. FIG. 6G shows a bottom view of the optical system 285 in FIG. 6A to illustrate the positions of the bonding pad 640, which are positioned to connect to the via 630 shown in FIG. 6F. The bonding pads 640 may have two parts connected by a wire buried in the layer 619.

Figure 7:
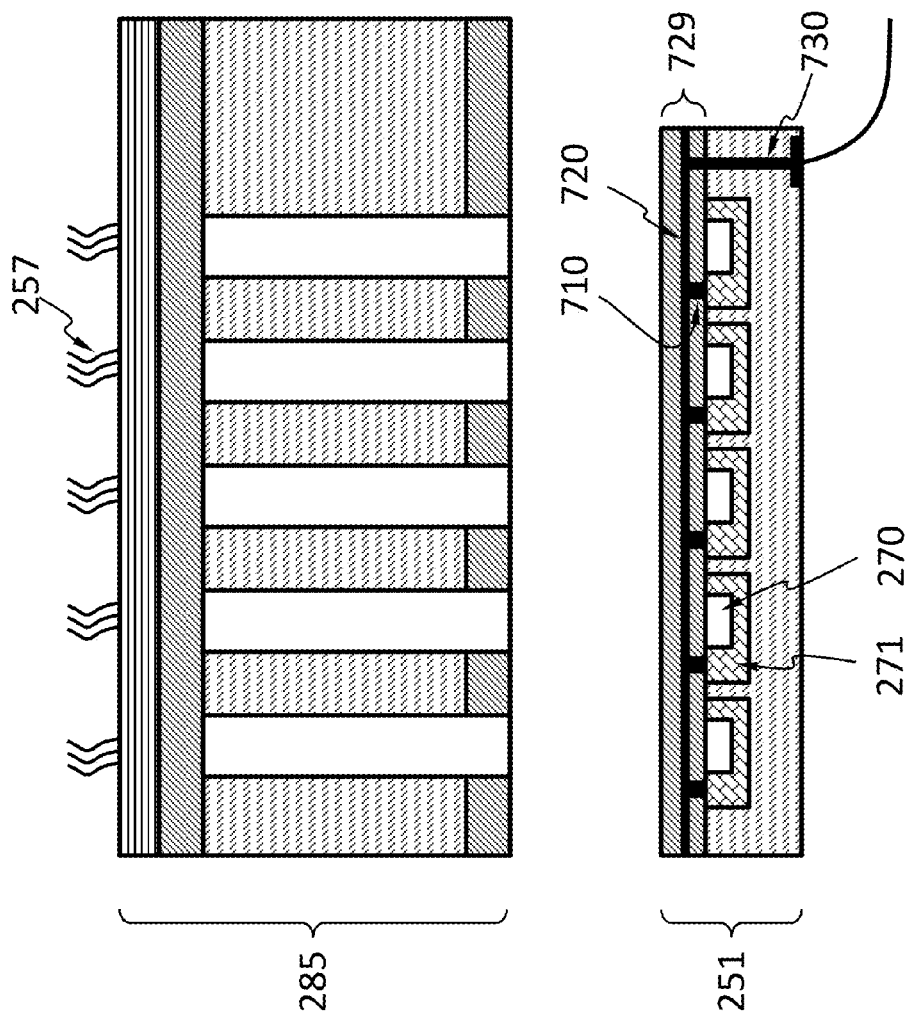
FIG. 7 schematically shows that a sensor in a microarray may have a redistribution layer with vias such as through-silicon vias (TSV) configured to electrically connect the transmission lines in the redistribution layer to bonding pads on the side opposite from the redistribution layer, according to an embodiment.

In an embodiment, schematically shown in FIG. 7, the sensor 251 has a redistribution layer 729. The redistribution layer 729 may have a plurality of vias 710 and a plurality of transmission lines 720. The redistribution layer 729 may have electrically insulation materials (e.g., silicon oxide) around the vias 710 and the transmission lines 720. The vias 710 electrically connect the control circuit 271 to the transmission lines 720. The redistribution layer 729 may also have vias 730 (e.g., through-silicon vias (TSV)) electrically connecting the transmission lines 720 to bonding pads 740 on the side opposite from the redistribution layer 729. This configuration shown in FIG. 7 allows the bonding pads 740 to be positioned away from the probes 257.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
 a sensor comprising pixels;
 collimators optically coupling to the pixels a signal generated by interaction between probes and an analyte;
 wherein at least one of the collimators comprises a core and a sidewall surrounding the core;
 wherein the core comprises a void space.

2. The apparatus of claim 1, further comprising a filter blocking at least a portion of an excitation radiation under which the signal is generated.

3. The apparatus of claim 2, wherein the filter is a dichroic filter.

4. The apparatus of claim 1, further comprising a transmissive layer.

5. The apparatus of claim 1, further comprising microlenses.

6. The apparatus of claim 1, wherein the collimators comprise a meta-material or a photonic crystal.

7. The apparatus of claim 1, wherein the signal is generated under excitation of an excitation radiation; wherein the core comprises a material essentially preventing an excitation radiation from passing through irrespective of propagation direction of the excitation radiation.

8. The apparatus of claim 1, wherein the signal is generated under excitation of an excitation radiation; wherein the core comprises a dichroic filter.

9. The apparatus of claim 1, wherein the core allows the signal to pass through essentially unabsorbed.

10. The apparatus of claim 1, wherein the sidewall attenuates a portion of the signal reaching the sidewall.

11. The apparatus of claim 1, wherein the sidewall is textured.

12. The apparatus of claim 2, wherein the filter comprises a meta-material or a photonic crystal.

13. The apparatus of claim 1, wherein the pixels are arranged in an array.

* * * * *